(12) United States Patent
Grelet et al.

(10) Patent No.: US 10,952,684 B2
(45) Date of Patent: Mar. 23, 2021

(54) METHOD FOR ESTIMATING THE PHYSICAL ACTIVITY OF AN UPPER LIMB

(71) Applicants: SYSNAV, Vernon (FR);
ASSOCIATION INSTITUT DE MYOLOGIE, Paris (FR)

(72) Inventors: Marc Grelet, Vernon (FR); Eric Dorveaux, Vernon (FR); David Vissiere, Paris (FR); Laurent Servais, Paris (FR); Jean-Yves Hogrel, Montrouge (FR); Amelie Moraux, Vernon (FR)

(73) Assignees: SYSNAV, Vernon (FR);
ASSOCIATION INSTITUT DE MYOLOGIE, Paris (FR)

( * ) Notice: Subject to any disclaimer, the term of this patent is extended or adjusted under 35 U.S.C. 154(b) by 269 days.

(21) Appl. No.: 16/073,187

(22) PCT Filed: Jan. 24, 2017

(86) PCT No.: PCT/FR2017/050147
§ 371 (c)(1),
(2) Date: Jul. 26, 2018

(87) PCT Pub. No.: WO2017/129890
PCT Pub. Date: Aug. 3, 2017

(65) Prior Publication Data
US 2019/0029605 A1 Jan. 31, 2019

(30) Foreign Application Priority Data
Jan. 27, 2016 (FR) ...................................... 1650652

(51) Int. Cl.
*A61B 5/22* (2006.01)
*A61B 5/11* (2006.01)
(Continued)

(52) U.S. Cl.
CPC .............. *A61B 5/7278* (2013.01); *A61B 5/11* (2013.01); *A61B 5/1114* (2013.01);
(Continued)

(58) Field of Classification Search
CPC ......................... A61B 5/224; A61B 5/11–1114
See application file for complete search history.

(56) References Cited

U.S. PATENT DOCUMENTS

2011/0207581 A1* 8/2011 Flaction ................... A61B 5/22
482/8
2015/0057128 A1* 2/2015 Ishii ....................... A61B 5/1114
482/8

(Continued)

FOREIGN PATENT DOCUMENTS

EP 2796123 A1 10/2014
FR 3042266 A1 4/2017

OTHER PUBLICATIONS

Flores et al., "Quantifying forearm and wrist joint power during unconstrained movements in healthy individuals," Journal of NeuroEngineering and Rehabilitation 2014, 11:157 (Year: 2014).*

(Continued)

*Primary Examiner* — Thaddeus B Cox
(74) *Attorney, Agent, or Firm* — Womble Bond Dickinson (US) LLP

(57) ABSTRACT

The present invention relates to a method for estimating the physical activity exerted by an upper limb (10) of a person (1), the method being characterised in that it comprises the steps of:
(a) Acquiring, by inertial measurement means (20) solidly attached to a forearm (11) of said upper limb (10) of said person (1), an angular speed of said forearm (11);
(b) Estimating, by data processing means (21, 31, 41), a torque exerted by the muscles of an arm (12) of the upper limb (1) on said forearm (11) as a function of the (Continued)

measured angular speeds, of an orientation of said forearm (11), and of physical parameters of said forearm (11);

(c) Determining, by the data processing means (21, 31, 41), a power exerted by the upper limb (10) as a function of the estimated torque and of the measured angular speed.

18 Claims, 3 Drawing Sheets

(51) Int. Cl.
    *G01L 5/00*          (2006.01)
    *A61B 5/00*          (2006.01)
    *G01C 9/00*          (2006.01)
    *G01C 21/12*        (2006.01)

(52) U.S. Cl.
    CPC ........... *A61B 5/1118* (2013.01); *A61B 5/1124* (2013.01); *A61B 5/224* (2013.01); *A61B 5/681* (2013.01); *A61B 5/6824* (2013.01); *G01C 9/00* (2013.01); *G01C 21/12* (2013.01); *G01L 5/0095* (2013.01); *A61B 2562/0219* (2013.01)

(56) References Cited

U.S. PATENT DOCUMENTS

2015/0374283 A1   12/2015   Walke et al.
2017/0311866 A1*  11/2017   Fuss ..................... A61B 5/0488

OTHER PUBLICATIONS https://en.wikipedia.org/wiki/Power_(physics) (Year: 2015).*
Preliminary Research Report and Written Opinion received for French Application No. 1650652, dated Jan. 17, 2017, 10 pages (1 page of French Translation Cover Sheet and 9 pages of original document).
Luinge, Hendrik Johannes, "Inertial Sensing of Human Movement", Twente University Press, 2002, pp. 1-87.
International Search Report and Written Opinion received for PCT Patent Application No. PCT/FR2017/050147, dated Apr. 20, 2017, 20 pages (10 pages of English Translation and 10 pages of Original Document).
International Preliminary Report on Patentability received for PCT Patent Application No. PCT/FR2017/050147, dated Aug. 9, 2018, 16 pages (9 pages of English Translation and 7 pages of Original Document).

* cited by examiner

US 10,952,684 B2

METHOD FOR ESTIMATING THE PHYSICAL ACTIVITY OF AN UPPER LIMB

GENERAL TECHNICAL FIELD

The present invention relates to the field of measuring the physical activity of the human body.

More precisely, it relates to a method for estimating the physical activity of an upper limb of a person via magneto-inertial techniques.

PRIOR ART

Numerous devices are proposed for sale for measuring the physical activity of a person using sensors sensitive to certain types of movements. An example that has existed for many years is the pedometer, the principle of which is to count the number of steps made by the wearer.

More recently, devices have been developed supplying more advanced information on physical activity than the simple counting of steps. It is possible for example to distinguish walking and running or instead to know the type of walking and the associated effort. Beyond the analysis of walking, some devices aim to take into account all of the movements made by the person in order for example to estimate the amount of energy used during an activity. To do so, one or more objects are worn by the person. Numerous configurations have been proposed concerning the wearing of these objects. For example, they can be worn on the wrist like a watch, placed in a pocket or on a belt, attached to the chest, to a leg, to a shoe, etc.

Measuring the physical activity of a person has varied applications. Many persons wish for example to increase or to regulate their energy expenditure notably for controlling body mass. In this framework, it may be useful to estimate the physical activity performed by these persons and to carry out a continuous monitoring over time. Some sportspersons may seek to optimise their training or simply to monitor the evolution of their performance. And, independently of a particular objective, everyone may be interested in their own physical condition level. Finally, in a medical framework, it may be essential to estimate and to monitor the evolution of the physical activity of a patient. For pathologies associated with muscular difficulties for example, the measurement of the physical activity is an indicator of the state of the patient. The physician can then monitor the evolution of the illness and evaluate the efficacy of a treatment. This can serve to demonstrate the validity of a treatment or to adapt it as a function of the response of the patient.

For the measurement of movements, some sensors frequently used in existing devices are acceleration sensors, angular speed sensors, magnetic field sensors, atmospheric pressure sensors, GPS position sensors, etc. Moreover, physiological measurements are sometimes carried out, such as for example heart beat or body temperature.

The first pedometers thus used a mechanical device sensitive to the movements created at each step. Most modern devices integrate however sensors equipped with electronic interfaces and often of MEMS type. MEMS components are derived from recent developments and their use is very widespread in the consumer electronics industry. The advantages of these sensors are the small size and a reduced energy consumption which makes it possible to integrate them within objects worn by a person without causing any particular bother. In addition, these components are available at costs compatible with consumer electronics and much cheaper than those of tactical components.

One difficulty with such devices relates to the reliability of the measurements carried out. Numerous indicators are given but their calculation is often not documented. And even if the calculation method is explained, the representativeness of the variable is not known. Even for simple variables such as the counting of steps, the performance is difficult to evaluate because the link with a physical effort is not direct, the step of a shuffle having nothing to do with that of a sprint race.

Methods are known for calculating in a clearly more precise manner relative displacement by integration of the sensors of an inertial unit. An inertial unit is constituted of at least three accelerometers and three gyrometers arranged in a triaxial way. Typically, gyrometers "maintain" a reference point, in which a double temporal integration of the measurements of the accelerometers makes it possible to estimate movement. However the inertial or magneto-inertial units necessary for this technique are heavy and expensive such as those carried on-board an airplane or a submarine and cannot be worn by a person. With MEMS type miniaturised sensors, the performance makes it possible to calculate a relative movement for a maximum duration of several seconds.

For this reason complementary or alternative methods have been proposed for finding one's bearings despite the limited performance of the sensors. It then involves using the information of additional sensors, it is possible to cite for example the measurement of the magnetic field gradient to estimate the speed or the use of video cameras to orient oneself with respect to the environment. The orientation with respect to the vertical direction may be obtained by measuring the gravity field, this device is sometimes called inclinometer. The course may be obtained by measuring the Earth's gravity field.

It may be observed however that these measurements remain noisy and poorly exploited.

The patent application FR1559591 has thus proposed a method for estimating the movement of a walking pedestrian thanks to inertial measurement means solidly attached to a lower limb of said pedestrian.

It would be desirable to have available a similar method for estimating the physical efforts carried out this time by an upper limb, and this is the subject matter of the present invention.

DESCRIPTION OF THE INVENTION

The present invention thus relates according to a first aspect to a method for estimating the physical activity exerted by an upper limb of a person, the method being characterised in that it comprises the steps of:
 (a) Acquiring, by inertial measurement means solidly attached to a forearm of said upper limb of said person, an angular speed of said forearm;
 (b) Estimating, by data processing means, a torque exerted by the muscles of an arm of the upper limb on said forearm as a function of the measured angular speed and of physical parameters of said forearm;
 (c) Determining, by the data processing means, a power exerted by the upper limb as a function of the estimated torque and of the measured angular speed.

According to other advantageous and non-limiting characteristics:
 the method comprises following step (a) a step (a1) of determining said orientation of the forearm;
 step (a) further comprises the acquisition by the inertial measurement means of a specific acceleration of said upper limb, the orientation of the forearm being determined as a function of the measured acceleration and angular speed;

the determination of the orientation of the forearm comprises the implementation of a linear or non-linear state estimation filter;

said inertial measurement means are arranged on said forearm between an elbow and a wrist;

the physical parameters of the forearm comprise a length of the forearm and a radius of the forearm;

the torque estimated at step (b) is a torque per unit of mass of said forearm given by the formula $$\vec{C_M} = \begin{pmatrix} \frac{R^2}{4} + \frac{L^2}{3} & 0 & 0 \\ 0 & \frac{R^2}{4} + \frac{L^2}{3} & 0 \\ 0 & 0 & \frac{R^2}{2} \end{pmatrix} \times \begin{bmatrix} \frac{d\omega_x}{dt} \\ \frac{d\omega_y}{dt} \\ \frac{d\omega_z}{dt} \end{bmatrix} - \frac{L}{2} g\cos\theta_e \vec{e_n},$$

where $\vec{\omega}$ is the measured angular speed, R the radius of the forearm, L the length of the forearm, $\vec{g}$ the acceleration due to gravity, $\theta_e$ the angle of elevation of the forearm and $\vec{e_n}$ the unit vector normal to the forearm and to the direction of the acceleration due to gravity;

the power exerted by the upper limb is determined at step (c) by the scalar product of the estimated torque and of the measured angular speed;

step (c) comprises the identification of the driving or resisting character of the determined power;

the method is a method for estimating a quantity representative of the physical activity exerted by the upper limb of the person, the method comprising a step (d) of estimating said physical quantity from the determined power;

said physical quantity is the energy exerted by the upper limb over a time interval, estimated at step (d) by adding together the absolute value of the powers determined at each instant of said time interval;

the method further comprises a step (e) of comparing said estimated physical quantity with at least one predetermined threshold so as to identify a muscular problem of the upper limb of the person.

According to a second aspect, the invention relates to equipment for the physical activity exerted by an upper limb of a person, characterised in that it comprises data processing means configured to implement:

A module for receiving an angular speed of a forearm of said upper limb of said person acquired by inertial measurement means solidly attached to said forearm;

A module for estimating a torque exerted by the muscles of an arm of the upper limb on said forearm as a function of the measured angular speed, of an orientation of said forearm, and of physical parameters of said forearm;

A module for determining a power exerted by the upper limb as a function of the estimated torque and of the measured angular speed.

According to other advantageous and non-limiting characteristics:

The equipment is a housing comprising the inertial measurement means;

The equipment further comprises means for attaching the housing to the upper limb, and communication means.

The equipment is a mobile terminal or a server, adapted to communicate with a housing comprising the inertial measurement means.

According to a third aspect, the invention relates to a system comprising the equipment according to the second aspect of the invention and at least one housing in connection.

According to a fourth and a fifth aspect, the invention relates to a computer programme product comprising code instructions for the execution of a method for estimating the physical activity exerted by an upper limb of a person according to the first aspect of the invention; and a storage means which can be read by computer equipment on which a computer programme product comprises code instructions for the execution of a method for estimating the physical activity exerted by an upper limb of a person according to the first aspect of the invention.

DESCRIPTION OF THE FIGURES

Other characteristics and advantages of the present invention will become clear on reading the description that follows of a preferential embodiment. This description will be given with reference to the appended drawings, in which.

DETAILED DESCRIPTION

Architecture

Figure 1:
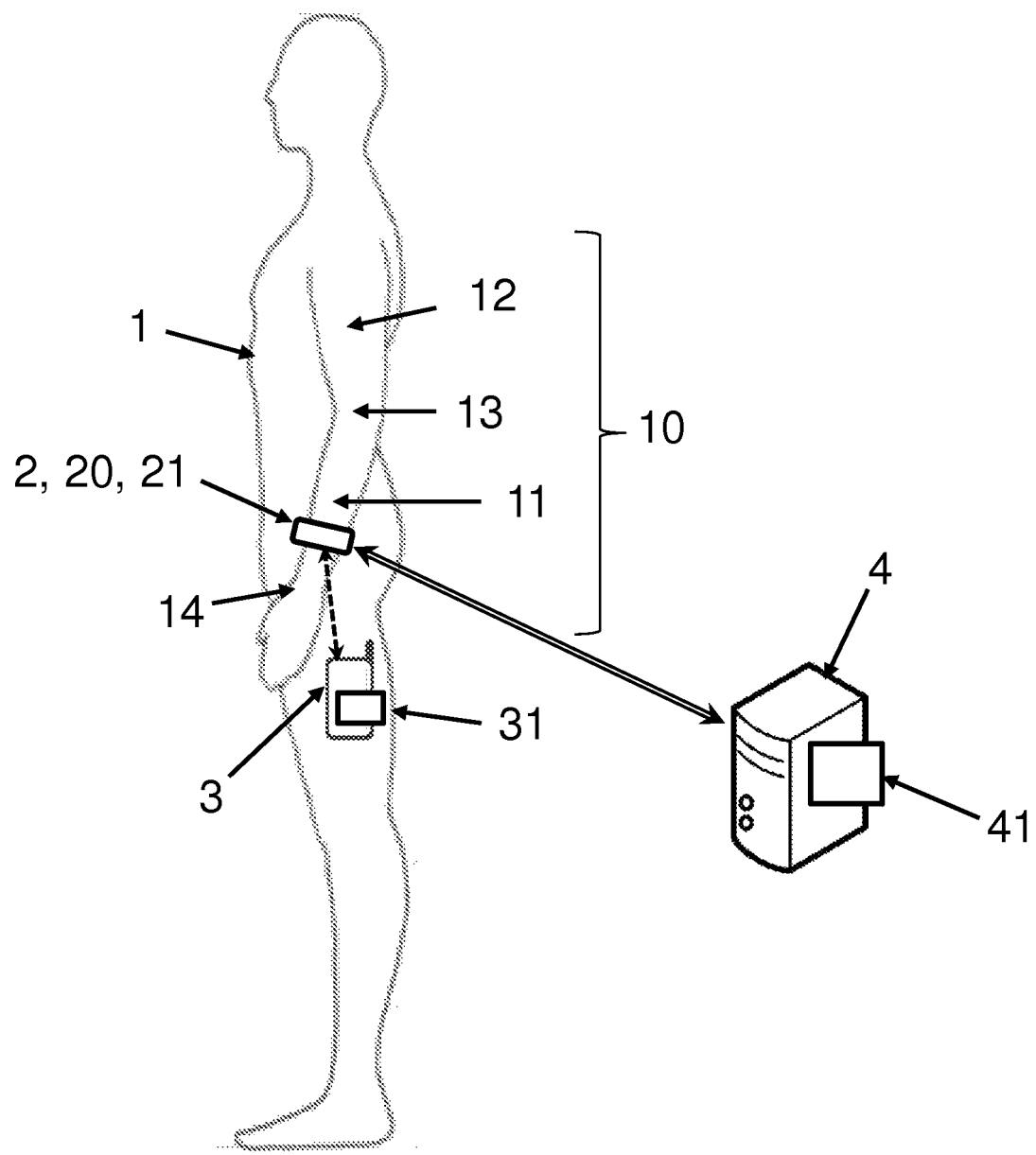
FIG. 1 is a diagram of items of equipment for the implementation of the method according to the invention.

With reference to FIG. 1, the present method enables the estimation of the physical activity exerted by an upper limb 10 of a person 1.

"Physical activity" is taken to mean a physical quantity representative of the efforts exerted by the muscles of the upper limb, the physical quantity being selected from a set of mechanical quantities such as the instantaneous power, the average power, the work, the energy, etc. These notions will be explained hereafter. Generally speaking, the present method may be defined as a method for estimating at least one physical quantity representative of the physical activity exerted by an upper limb 10 of a person 1.

The person 1 has at least one upper limb 10 (i.e. an "arm" in everyday language, even if as will be seen later this term is inappropriate, an arm anatomically designating "upper arm", that is to say the part between the shoulder and the elbow) equipped with inertial measurement means 20. It will be understood that each of the two upper members 10 of the person 1 may be equipped with inertial measurement means 20.

The upper limbs 10 are each constituted of three segments: the arm 12, the forearm 11 and the hand. The articulation of the elbow 13 connects the arm to the forearm, and the wrist 14 connects the forearm to the hand.

More precisely, the inertial measurement means 20 are solidly attached to the forearm 11, i.e. that they have a substantially identical movement in the terrestrial reference frame, it will be seen how later. The inertial measurement means are more precisely arranged between the elbow 13 and the wrist 14 of the person (included), and generally speaking any emplacement having with respect to the elbow 13 of the upper limb 10 substantially uniquely a rotational movement, that is to say due to a lever arm.

The distance between the elbow 13 and the means 20 are of little importance as will be seen, the person is able to fasten it near to the wrist 14 for more distance between the elbow 13 and the means 20 and thus more precision, but whatever its position the present method works.

As will be seen hereafter, physical parameters of said forearm 11 are necessary, in particular anthropometric parameters of which a length of the forearm 11 and a radius of the forearm 11.

These quantities may be input parameters (keyed in by the person 1) or then an average value may be used. It is noted that the radius intervenes in the calculation but as will be seen it may be ignored because the term linked to the radius is small compared to the other terms.

Furthermore, the mass of the forearm 11 may be used, but it is possible to provide normalised values of the quantities representative of the physical activity (i.e. per unit of mass of the forearm 11), which means that the knowledge thereof is optional.

Figure 2:
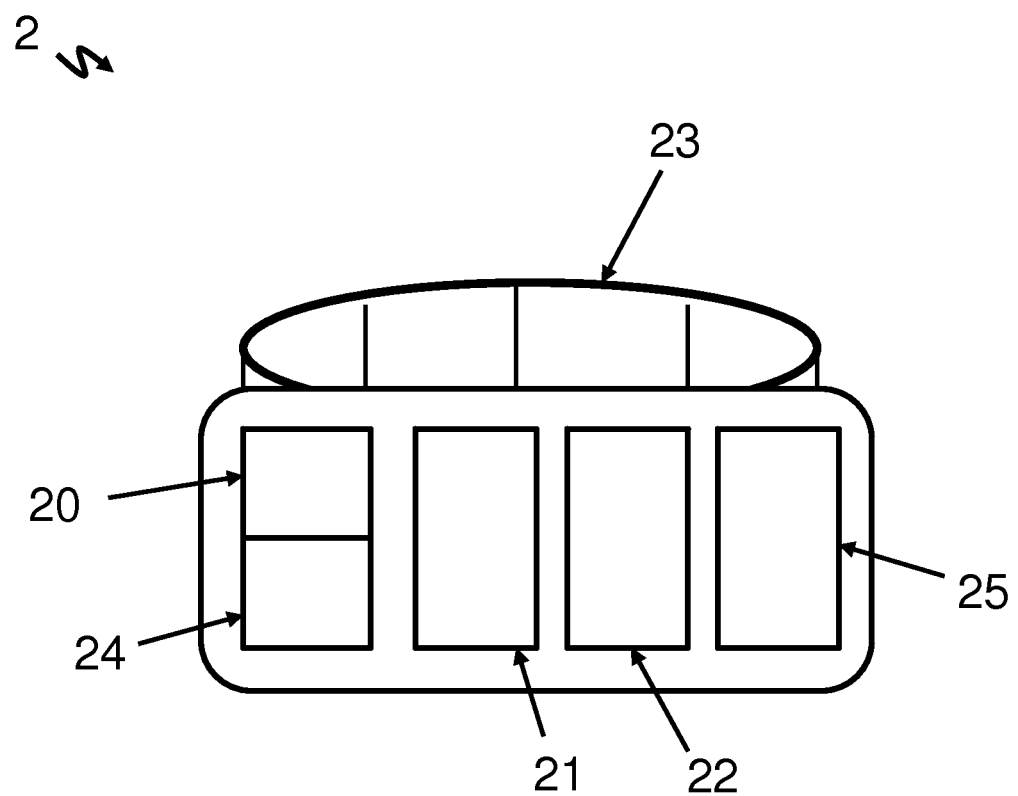
FIG. 2 represents in greater detail an example of housing for the implementation of the method according to the invention.

The inertial measurement means 20 are preferentially those of a housing 2 such as represented in FIG. 2 having means 23 for attachment to the upper limb 10. These attachment means 23 consist for example of a bracelet for example with a hook and loop fastening strip which clasps the limb and enables an integral connection. As will be seen later, it is in fact desirable that the inertial measurement means 20 are arranged as close as possible to the wrist 14, and if possible cannot move along the limb 10.

Inertial measurement means 20 is taken to mean an inertia unit comprising at least three accelerometers and three gyrometers arranged in a triaxial way. The gyrometers measure the instantaneous angular speed of the inertial unit with respect to the terrestrial reference frame, noted (73. The accelerometers are sensitive to external forces other than gravitational forces applied to the sensor, and make it possible to measure an acceleration noted $\vec{\gamma}$. As will be seen, the means 20 may comprise means 24 for acquiring the orientation (of which the angular speed is the derivative) or even in a more limited manner only the angle of elevation (i.e. a single component of the orientation) of the forearm 11. For example an inclinometer, which is often a simple accelerometer, does not make it possible to estimate the orientation or the angular speed of the forearm 11 but only the angle of elevation and with greater errors than with a complete inertial unit. It is to be noted that in one embodiment where only the angle of elevation is measured thanks to a simple inclinometer, this data may be "de-noised" thanks to the angular speed measurements of the means 20. It will be understood however that the complete orientation may be measured by suitable means 24, for example optical or magnetic. As will be seen, the means 24 (whether they measure one component or all the orientation) are not indispensable and only means for inertial measurement of the angular speed are essential.

The housing 2 may comprise processing means 21 (typically a processor) for directly implementing in real time the processing operations of the present method, or instead the measurements may be emitted via communication means 25 to an external device such as a mobile terminal (smartphone) 3, or even a remote server 4, or instead the measurements may be recorded in local data storage memory means 22 (for example a flash type memory) for an a posteriori processing for example on the server 4.

The communication means 25 may implement a short-range wireless communication for example Bluetooth or Wifi (in particular in one embodiment with a mobile terminal 3) or even be means for connecting to a mobile network (typically UMTS/LTE) for a long distance communication. It should be noted that the communication means 25 may be for example a wired connector (typically USB) for transferring data from the local data storage means 22 to those of a mobile terminal 3 or a server 4.

If it is a mobile terminal 3 (respectively a server 4) which hosts "the intelligence", it comprises processing means 31 (respectively 41) such as a processor for the implementation of the processing operations of the present method that are going to be described. When the processing means used are those 21 of the housing 2, said housing may further include communication means 25 for transmitting the estimated position. For example the position of the wearer may be sent to the mobile terminal 3 to display the position in an interface of browsing software.

In the remainder of the present description, it will be seen that the data processing means 21, 31, 41 respectively of the housing 2, of a smartphone 3 and of a remote server 4, may indiscriminately and according to the applications carry out all or part of the steps of the method.

Principle and Notations

In a first step (a), the method comprises the acquisition by the inertial measurement means 20 of at least the angular speed $\vec{\omega}$ of said upper limb 10, and more precisely of the forearm 11.

In a preferred manner, the specific acceleration $\vec{\gamma}$ of the forearm 11 is also measured. Advantageously, the method comprises following step (a) a step (a1) of determining, by the data processing means 21, 31, 41, said orientation of the forearm 11, and does so thanks to this measured acceleration (and the measured angular speed).

It should be noted that in the remainder of the description, when acceleration/speed/orientation of the upper limb 10 is mentioned, it is understood at the level of the inertial measurement means 20, because points of the upper limb 10 situated for example at the level of the arm 12 will have a different movement.

A terrestrial inertial reference frame $(R_i)$ is introduced, as well as a reference frame $(R_b)$ having for origin the centre of the housing 2 and of which the axes are linked to those of the housing 2. The angular speed $\vec{\omega}$ of the forearm 11 is equal to the rotation of $(R_b)$ with respect to $(R_i)$. The specific acceleration is equal to the sum of the acceleration of the housing in the terrestrial inertial reference frame less the value of the gravity field $\vec{g}$. Gyrometer and accelerometer inertial sensors (inertial measurement means 20) measure respectively $\vec{\omega}$ and $\vec{\gamma}$ expressed in the reference point $(R_b)$.

These quantities are advantageously measured with a dt sampling (i.e. every "dt" seconds) with dt very small in view of the characteristic time of the movements of the person 1, typically 10 ms.

The orientation of the means 20 with respect to the terrestrial inertial reference frame may be given for example by a rotation matrix (noted R), an attitude quaternion (noted q), the attitude is synonymous with orientation in space or Euler angles (roll $\varphi$, pitch $\theta$, yaw $\psi$). These three representations are equivalent, they are thus used indiscriminately in this document.

The initialisation of the attitude may be done for example from acceleration measurements (and if need be measurements of an optional magnetometer) by considering that the limb 10 and thus the means 20 are immobile at the start up and that the magnetic field is equal to the terrestrial magnetic field. In this case, the measured acceleration is equal to the opposite of the gravitational field $\vec{\gamma} = -\vec{g}$. One then has the roll and the pitch with the following formulas:

$$\varphi = -\tan^{-1} \frac{\gamma_y}{\gamma_z}$$

$$\theta = \sin^{-1} \frac{\gamma_x}{\sqrt{\gamma_x^2 + \gamma_y^2 + \gamma_z^2}}$$

The magnetic course may then be calculated from the measurement of the magnetic field with the formula:

$$\psi = \tan^{-1} \frac{B_z \cdot \sin\varphi - B_y \cdot \cos\varphi}{B_x \cdot \cos\theta + B_y \cdot \sin\theta \cdot \sin\varphi + B_z \cdot \sin\theta \cdot \cos\varphi}$$

The formula giving the transfer matrix of the terrestrial reference frame ($R_i$) to the reference frame ($R_b$) of the means 20 from the Euler angles is:

$$R_{R_i \to R_b} = \begin{bmatrix} \cos\theta \cdot \cos\psi & -\cos\theta \cdot \sin\psi & \sin\theta \\ \cos\psi \cdot \sin\theta \cdot \sin\varphi + \cos\varphi \cdot \sin\psi & \cos\varphi \cdot \cos\psi - \sin\theta \cdot \sin\varphi \cdot \sin\psi & -\cos\theta \cdot \sin\varphi \\ \sin\varphi \cdot \sin\psi - \cos\varphi \cdot \cos\psi \cdot \sin\theta & \cos\psi \cdot \sin\varphi + \cos\varphi \cdot \sin\theta \cdot \sin\psi & \cos\theta \cdot \cos\varphi \end{bmatrix}$$

The above formula makes it possible to estimate the orientation of the housing 2 at any moment from acceleration and angular speed measurements but an important limitation comes from the hypothesis of immobility ($\vec{\gamma} = -\vec{g}$). In practice, the forearm 11 moves and the acceleration is not negligible in view of the value of the gravity field. For this reason, it is opportune to use angular speed measurements to filter errors linked to accelerations undergone by the housing 2.

In other words, the determination of the orientation of the forearm 11 advantageously comprises the implementation of a linear or non-linear state estimation filter.

Methods making it possible to estimate the orientation of an inertial unit are known. To do so, it is possible to use a linear (Luenberger filter, Kalman filter, etc.) or non-linear (extended Kalman filter, invariant observer, etc.) state estimation filter. In the present description, the main steps of the extended Kalman filter are recalled, but those skilled in the art will know how to transpose to other filters.

In an extended Kalman filter, the state is represented by a vector for example a 4-dimensional attitude quaternion. It is possible to add other states to this vector to improve the estimation, for example the bias of the sensors. A covariance matrix is used to estimate the covariance between each state of the filter, it is of dimension n² thus of dimension 16 in the example of the attitude quaternion. The Kalman filter takes place in two steps, a prediction step and an updating step. During the updating, a Kalman $K_n$ gain is calculated from the covariance matrix.

The prediction step is based on a model linked to the angular speed $\vec{\omega}$. The differential equation is used on the transfer matrix $R_{R_0 \to R}$, and the coordinates of ω expressed in the base of the housing 2.

$$\dot{R}_{R_i \to R_b} = \begin{bmatrix} 0 & -\omega_{bz} & \omega_{by} \\ \omega_{bz} & 0 & -\omega_{bx} \\ -\omega_{by} & \omega_{bx} & 0 \end{bmatrix} \times R_{R_i \to R_b}$$

By considering that the period of the sampling noted dt is sufficiently small, the approximation of a development limited to the first order is used:

$$R_{R_i \to R_b}(t+dt) = R_{i \to b}(t) + \dot{R}_{i \to b}(t)dt$$

By noting $\hat{R}_n$ the estimation of the matrix $R_{R_i \to R_b}$ after n sample steps, the estimation of the matrix $\hat{R}_n$ for each measurement $\vec{\omega}_n$ is:

$$\hat{R}_{n+1} = \hat{R}_n + \begin{bmatrix} 0 & -\omega_{n,z} & \omega_{n,y} \\ \omega_{n,z} & 0 & -\omega_{n,x} \\ -\omega_{n,y} & \omega_{n,x} & 0 \end{bmatrix} \times \hat{R}_n dt$$

The equation is given here for a rotation matrix but an equivalent differential equation exists between attitude quaternion and angular speed. In parallel, the covariance matrix is modified by linearizing the differential equation.

The updating step relies on the measurement of the accelerometer. One uses the fact that the acceleration of the housing 2 is equal to the sum of the specific acceleration measured by the means 20 and the gravity field.

$$\vec{\alpha} = \vec{\gamma} + \vec{g}$$

It is known in addition that the acceleration $\vec{\alpha}$ is on average zero (it is understood that the upper limb 10 regularly returns to its starting position and that the movements in one direction or the other compensating each other statistically). One deduces therefrom that $\vec{\gamma}$ expressed in the terrestrial inertial reference point is equal on average to $-\vec{g}$.

From the rotation matrix $\hat{R}_n$ and measurements of the means 20 in the reference point of the housing 2, the specific acceleration may be expressed in the terrestrial inertial reference point:

$$\hat{R}_n^{-1} \begin{bmatrix} \gamma_{n,x} \\ \gamma_{n,y} \\ \gamma_{n,z} \end{bmatrix}$$

The difference between the estimated gravity field and the real terrestrial gravity field is then written:

$$\text{error}_n = \hat{R}_n^{-1} \begin{bmatrix} \gamma_{n,x} \\ \gamma_{n,y} \\ \gamma_{n,z} \end{bmatrix} - \begin{bmatrix} 0 \\ 0 \\ g \end{bmatrix}$$

This difference is used for resetting the attitude during the updating step. By linearizing this formula, it is possible to calculate the Kalman gain and thereafter to update the state and the covariance matrix.

The updating of the covariance matrix is based on the hypothesis that the errors due to the sensors and to the approximations are modelled as a Gaussian distribution noise. The variance is estimated by measuring the noise of the sensors at rest and from hypotheses on the movements made by the forearm 11.

It is thus possible for the data processing means 21, 31, 41 to estimate the orientation of the housing 2 (thanks to the measurements of acceleration and of angular speed of the means 20) and consequently that of the forearm 11. It will be understood that any other device 24 enabling this measurement could also be used, noting however that an inclinometer alone measuring the angle of elevation does not give all the orientation (for example the torsion of the forearm 11 is not given), to do so at least one gyrometer of the means 20 is necessary. In the remainder of the description of this invention, it suffices that the orientation of the forearm 11 is available or even that the angle of elevation between the forearm 11 and the horizontal direction is known (with precision).

Torque Against Universal Gravity

In a step (b), the data processing means 21, 31, 41 estimate a torque exerted by the muscles of an arm 12 of the upper limb 1 on said forearm 11 as a function of the measured angular speeds, of an orientation of said forearm 11, and of physical parameters of said forearm 11. As explained, this torque may be a specific torque.

Figure 3:
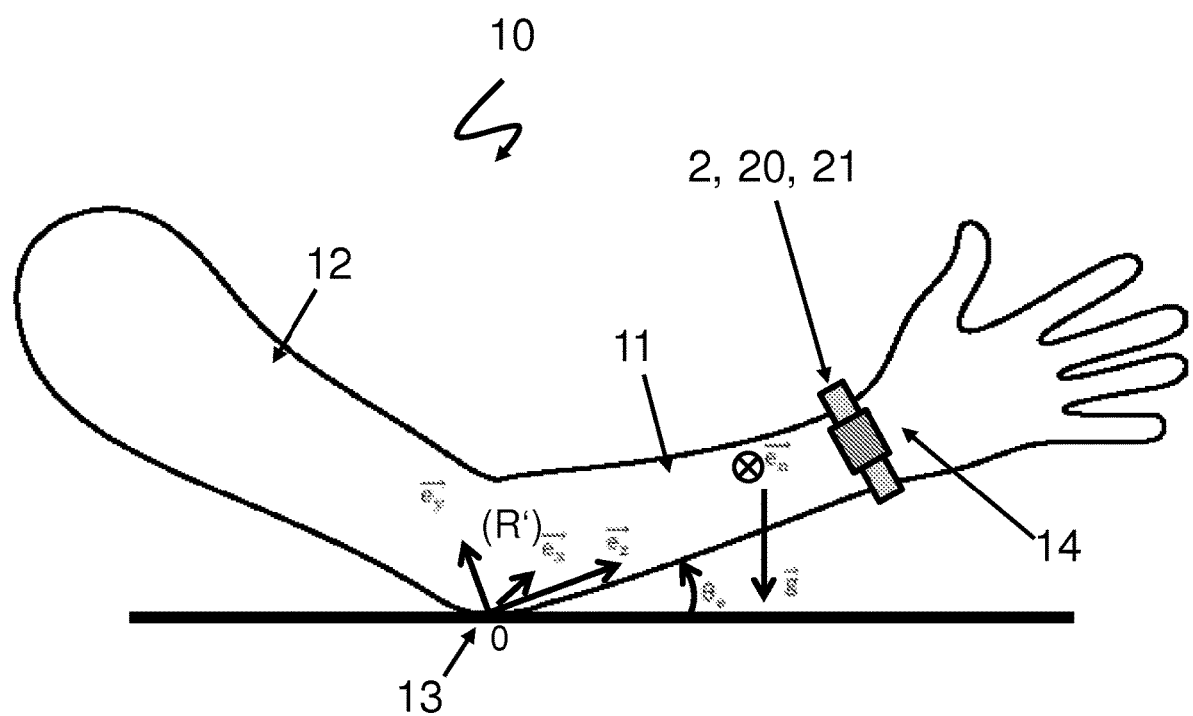
FIG. 3 schematically represents an upper limb equipped with a housing for the implementation of the method according to the invention.

To do so, it is observed that in seated position it is natural to have the elbow 13 set down on a support, for example a table, an armrest, etc., as represented in FIG. 3. A large part of the activity next consists in displacing the forearm 11 in a rotational movement around the contact point between the elbow and the support. It may be noted that the frailest persons, notably on account of muscular disorders, spend the majority of their time seated in an armchair with their elbow set down on a support. The most mobile persons also spend a lot of time with their elbows set down on a support, for example a desk, in addition it is possible to identify these periods from inertial measurements.

The forearm 11 is modelled as a cylinder of length L, of radius R and specific gravity $\rho$, forming as explained the physical parameters of the forearm 11. It is assumed that the elbow 13 is set down on the armrest of the armchair and the contact point is noted O. The rotations of the forearm 11 around the contact point are considered. The reference frame $(R_O)$ having for origin O and of which the axes are those of a terrestrial reference frame is used, as well as the reference frame (R') having for origin O and of which the axes are linked to those of the forearm 11. The angular speed $\vec{w}$ of the forearm 11 is equal to the rotation of $(R_O)$ with respect to (R').

The speed of a point of the forearm 11 M in $(R_O)$ is given by:

$$\vec{v}_M = \vec{\omega} \wedge \vec{OM}$$

And by definition, the kinetic moment of the forearm with respect to O is:

$$\vec{L}_O = \iiint \vec{OM} \wedge \rho \vec{v}_M d\tau = \rho \iiint \vec{OM} \wedge (\vec{\omega} \wedge \vec{OM}) d\tau$$

By noting $\rho$ the specific gravity and by integrating on the volume of the forearm 11.

In cylindrical coordinates $(\vec{e}_r, \vec{e}_\theta, \vec{e}_z)$, with $\vec{e}_z$ in the axis of the forearm 11, this gives:

$$\vec{L}_O = \rho \int_0^L \int_0^{2\pi} \int_0^R (r\vec{e}_r + z\vec{e}_z) \wedge (\vec{\omega} \wedge (r\vec{e}_r + z\vec{e}_z)) r d_r d_\theta d_z$$

$$\vec{L}_O = \rho \int_0^L \int_0^{2\pi} \int_0^R ((r^2+z^2)\vec{\omega} - (\vec{\omega} \cdot (r\vec{e}_r + z\vec{e}_z))(r\vec{e}_r + z\vec{e}_z)) r d_r d_\theta d_z$$

By using $\vec{e}_r = \cos\theta \vec{e}_x + \sin\theta \vec{e}_y$ one obtains:

$$\vec{L}_O = \rho \int_0^L \int_0^{2\pi} \int_0^R ((r^2+z^2)\vec{\omega} - (\omega_x r \cos\theta + \omega_y r \sin\theta + \omega_z z)(r \cos\theta \vec{e}_x + r \sin\theta \vec{e}_y + z\vec{e}_z)) r d_r d_\theta d_z$$

By projecting on the axis $\vec{e}_z$ $$L_{Oz} = \rho \int_0^L \int_0^{2\pi} \int_0^R ((r^2+z^2)\omega_z - (\omega_x r \cos\theta + \omega_y r \sin\theta + \omega_z z) z) r d_r d_\theta d_z$$

$$L_{Oz} = \rho \int_0^L \int_0^{2\pi} \int_0^R (r^3 \omega_z - \omega_x r^2 z \cos\theta - \omega_y r^2 z \sin\theta) d_r d_\theta d_z$$

After integration, there remains:

$$L_{Oz} = \frac{\rho 2\pi L R^4 \omega_z}{4} = \frac{m R^2 \omega_z}{2}$$

Similarly, by projecting on the axis $\vec{e}_x$ $$L_{Ox} = \rho \int_0^L \int_0^{2\pi} \int_0^R ((r^2+z^2)\omega_x - (r\omega_x \cos\theta + r\omega_y \sin\theta + \omega_z z) r \cos\theta) r d_r d_\theta d_z$$

$$L_{Ox} = \rho \int_0^L \int_0^{2\pi} \int_0^R ((r^3 \sin^2\theta + rz^2)\omega_x - r^3 \cdot \omega_y \sin\theta \cos\theta - \omega_z r^2 z \cos\theta) d_r d_\theta d_z$$

After integration, there remains:

$$L_{Ox} = \rho \Omega_x \left( \frac{\pi L R^4}{4} + \frac{2\pi L^3 R^2}{6} \right) = \left( \frac{R^2}{4} + \frac{L^2}{3} \right) m \omega_x$$

By symmetry, the same calculation gives for the axis $$L_{Oy} = \left( \frac{R^2}{4} + \frac{L^2}{3} \right) m \omega_y$$

In the reference point of origin O and axes $(\vec{e}_x, \vec{e}_y, \vec{e}_z)$ with $\vec{e}_z$ in the axis of the forearm 11 (see FIG. 3), the mass inertia tensor may thus be written:

$$\bar{I} = \begin{pmatrix} \frac{R^2}{4} + \frac{L^2}{3} & 0 & 0 \\ 0 & \frac{R^2}{4} + \frac{L^2}{3} & 0 \\ 0 & 0 & \frac{R^2}{2} \end{pmatrix}$$

$$\vec{L}_O = m \bar{I} \vec{\omega}$$

By definition, the moment of the gravitational forces on the forearm 11 with respect to O is written:

$$\vec{M}_{PO} = \iiint \vec{OM} \wedge \vec{g} \rho d\tau$$

In cylindrical coordinates $(\vec{e}_r, \vec{e}_\theta, \vec{e}_x)$ with $\vec{e}_z$ in the axis of the forearm 11, this gives:

$$\vec{M_{PO}} = (\int_0^L \int_0^{2\pi} \int_0^R (r\vec{e}_r + z\vec{e}_z)\rho r\, dr\, d\theta\, dz) \wedge \vec{g}$$

$$\vec{M_{PO}} = (\rho \pi R^2 \int_0^L z\, dz)\vec{e}_z \wedge \vec{g} + (\rho \int_0^L \int_0^{2\pi} \int_0^R r^2 \vec{e}_r\, dr\, d\theta\, dz) \wedge \vec{g}$$

The second term of the sum is zero (using an argument of symmetry) and one obtains after integration and simplifications:

$$\vec{M_{PO}} = m\frac{L}{2} \vec{e}_z \wedge \vec{g}$$

By introducing the angle of elevation $\theta_e$ and the unit vector $\vec{e}_n$ normal to the forearm 11 and to the direction of the gravity field as defined in the figure, one has $\vec{e}_z \wedge \vec{g} = \cos\theta_e \vec{e}_n$ $$\vec{M_{PO}} = m\frac{L}{2} g \cos\theta_e \vec{e}_n$$

The kinetic moment theorem is then used by considering that the only forces applied to the forearm are its weight and the forces of the muscles. By noting $\vec{M_{BrasO}}$ the moment of the forces exerted by the muscles of an arm 12 on the forearm 11, one has:

$$\frac{d\vec{L_O}}{dt} = \vec{M_{PO}} + \vec{M_{BrasO}}$$

$$\vec{M_{BrasO}} = \frac{d\vec{L_O}}{dt} - \vec{M_{PO}} = m\bar{I}\frac{d\vec{\omega}}{dt} - m\frac{L}{2}g\vec{e}_z \wedge \vec{g}$$

Finally, one notes $\vec{C_M}$ the torque to exert to lift the forearm 11 divided by its mass and one obtains:

$$\vec{C_M} = \bar{I}\frac{d\vec{\omega}}{dt} - \frac{L}{2}g\cos\theta_e \vec{e}_n$$

$$\vec{C_M} = \begin{pmatrix} \frac{R^2}{4} + \frac{L^2}{3} & 0 & 0 \\ 0 & \frac{R^2}{4} + \frac{L^2}{3} & 0 \\ 0 & 0 & \frac{R^2}{2} \end{pmatrix} \times \begin{bmatrix} \frac{d\omega_x}{dt} \\ \frac{d\omega_y}{dt} \\ \frac{d\omega_z}{dt} \end{bmatrix} - \frac{L}{2}g\cos\theta_e \vec{e}_n$$

$$\vec{C_M} = \begin{bmatrix} \left(\frac{R^2}{4} + \frac{L^2}{3}\right)\frac{d\omega_x}{dt} \\ \left(\frac{R^2}{4} + \frac{L^2}{3}\right)\frac{d\omega_y}{dt} \\ \frac{R^2}{2}\frac{d\omega_z}{dt} \end{bmatrix} - \frac{L}{2}g\cos\theta_e \vec{e}_n$$

As explained, it is possible to ignore the term concerning the radius in view of the term concerning the length, and to estimate the torque more simply by the formula:

$$\vec{C_M} = \begin{bmatrix} \frac{L^2}{3}\frac{d\omega_x}{dt} \\ \frac{L^2}{3}\frac{d\omega_y}{dt} \\ 0 \end{bmatrix} - \frac{L}{2}g\cos\theta_e \vec{e}_n$$

This formula may be further simplified as $$\vec{C_M} = -\frac{L}{2}g\cos\theta_e \vec{e}_n$$

by ignoring the term concerning the length, for example in one embodiment where only an inclinometer 24 and means 20 capable of measuring the angular speed (gyrometers) are available, so as to calculate the torque uniquely from the angle of elevation. Such a value would however be approximate and it appears imperative to filter the errors of the angle of elevation with the measured angular speeds to use this formula.

In a step (c), the data processing means 21, 31, 41 determine a power exerted by the upper limb 10 as a function of the estimated torque and of the measured angular speed.

More precisely, the (instantaneous) power is given by the scalar product of the estimated torque and of the angular speed. In other words, it is equal to the torque multiplied by the angular speed. It is possible if need be to again normalise by the mass of the forearm 11 and the specific power is equal to:

$$P_M = \vec{C_M} \cdot \vec{\omega} = \bar{I}\frac{d\vec{\omega}}{dt} \cdot \vec{\omega} - \frac{L}{2}g\cos\theta_e \vec{e}_n \cdot \vec{\omega}$$

$$P_M = \bar{I}\frac{d\vec{\omega}}{dt} \cdot \vec{\omega} + \frac{L}{2}g\cos\theta_e \frac{d\theta_e}{dt}$$

And by using the projections on the axes linked to the housing:

$$P_M = \begin{pmatrix} \frac{R^2}{4} + \frac{L^2}{3} & 0 & 0 \\ 0 & \frac{R^2}{4} + \frac{L^2}{3} & 0 \\ 0 & 0 & \frac{R^2}{2} \end{pmatrix} \frac{d(\omega_x^2 + \omega_y^2 + \omega_z^2)}{dt} + \frac{L}{2}(g_y\omega_x - g_x\omega_y)$$

As before, this power may be calculated more easily by ignoring R in view of L, or even by ignoring L.

It is observed that in all cases the power associated with the torque exerted by the arm 12 on the forearm 11 is the sum of two terms. The first term comes from the kinetic energy making it possible to place the forearm 11 in movement. The second term comes from the potential energy linked to the height of the forearm 11. It may be observed that the second term, which derives from a potential energy, may be expressed uniquely from the angle of elevation. Devices uniquely supplying the elevation may thus benefit from this method.

The power may be of negative sign when the forearm 11 is lowered or when its angular speed decreases. Even in these cases the muscles have to provide an effort to retain the limb. In a preferred manner, step (c) comprises the identification of the driving or resisting character of the determined power, in particular as a function of the sign of the angular speed and of the orientation (closing of the upper limb 10 for a driving movement and opening of upper limb 10 for a resisting movement).

Several models may be envisaged for estimating as best as possible the effort exerted by the muscles in this type of movement. It is possible to consider only movements having a positive power because they are the movements demanding the most energy from the muscles. Or instead the absolute value of the power could be considered by applying potentially a different coefficient as a function of the sign of each term constituting the power. This makes it possible to reflect the different types of efforts made by the muscles.

The power may be the requested quantity and said quantity may be directly returned/stored by the housing 2 or another equipment such as the terminal 3. It is noted that the average power may be calculated over a journey, if need be the average power of the positive powers, or instead the average of the absolute value of powers.

In a step (d), the data processing means 21, 31, 41 can determine another quantity representative of the physical activity of the upper limb 10 from the power.

For example the work carried out by the muscles of the arm during each movement may be estimated from the power of the torque exerted by the arm 12 on the forearm 11, by adding together for each sample the specific power in order to know the specific work of the muscles during the considered period (the work may be negative).

Alternatively, an energy exerted by the upper limb over a time interval by adding together the absolute value of the powers determined at each instant of said time interval.

In a preferred manner, the method further comprises a step (e) of comparing said estimated physical quantity with at least one predetermined threshold so as to identify a muscle problem of the upper limb 10 of the person 1. This may be a minimum threshold (for example, if the muscle of the forearm is not capable of exceeding a specific power value, the patient may suffer from muscle degeneration) but also a maximum threshold (for example, chorea type illnesses are defined by the onset of uncontrollable, sudden and irregular movements).

Equipment and System

According to a second aspect, the invention in particular relates to the equipment 2, 3, 4 for the implementation of one or the other of the embodiments of the method.

As explained previously, according to a first embodiment the equipment is an autonomous housing 2 comprising the inertial measurement means 20 and the data processing means 21 configured for the implementation of the steps of the method.

The housing 2 further comprises means 23 for attaching the housing 2 to the upper limb 10, and if need be a magnetometer 24, data storage means 22 (for the storage of measured accelerations/angular speeds or estimated physical quantities) and/or communication means 25 for the exportation of the results.

According to a second embodiment, the equipment is a mobile terminal 3 or a server 4, adapted to communicate with a housing 2 comprising the inertial measurement means 20. In other words, the terminal 3 or the server 4 comprises the processing means 31 or 41 configured for the implementation of the steps of the method. Each housing 2 may all the same comprise data processing means 21 for the control of the means 20 and the transmission (via communication means 25) of the measured data to the data processing means 31, 41.

It should be noted that the means 21, 31, 41 may if need be share the steps of the method. For example, in the case of a medical application, the processing means 21 of the housing 2 can carry out the steps up to (c), and a posteriori the means 41 of the server 4 implement step (d) of determining a suitable physical quantity so as to identify a potential disorder of the movement of the person 1.

The invention also relates to in this case the system comprising the equipment 3, 4 according to this embodiment and the "satellite" housing or housings 2 in connection.

In all cases, the data processing means 21, 31, 41 of the "main" items of equipment 2, 3, 4 are configured to implement:

A module for receiving an angular speed of a forearm 11 of said upper limb 10 of said person 1 (and if need be the acceleration of the forearm 11) acquired by inertial measurement means 20 solidly attached to said forearm 11;

Optionally, a module for determining an orientation of the forearm 11, in particular as a function of the acceleration and of the measured angular speeds;

A module for estimating a torque exerted by the muscles of an arm 12 of the upper limb 10 on said forearm 11 as a function of the measured angular speeds, of the orientation of said forearm 11, and of physical parameters of said forearm 11;

A module for determining a power exerted by the upper limb 10 as a function of the estimated torque and of the measured angular speed.

Computer Programme Product

According to a third and a fourth aspect, the invention relates to a computer programme product comprising code instructions for the execution (on the processing means 21, 31, 41) of the physical activity exerted by an upper limb 10 of a person 1 according to the first aspect of the invention, as well as storage means which can be read by computer equipment (for example data storage means 22) on which this computer programme product is found.

The invention claimed is:

1. Method for estimating a physical activity exerted by an upper limb of a person comprising:
   (a) Acquiring, by inertial measurement means solidly attached to a forearm of said upper limb of said person, a measured angular speed of said forearm;
   (b) Estimating, by data processing means, a torque exerted by any muscles of an arm of the upper limb on said forearm as a function of the measured angular speed, of an orientation of said forearm, and of physical parameters of said forearm;
   (c) Determining, by the data processing means, a power exerted by the upper limb estimated from the scalar product of the estimated torque and of the measured angular speed.

2. The method according to claim 1, comprising after said acquiring, determining said orientation of the forearm.

3. The method according to claim 2, wherein said acquiring further comprises acquisition by the inertial measurement means of a measured acceleration of said upper limb, the orientation of the forearm being determined as a function of the measured acceleration and the angular speed.

4. The method according to claim 3, wherein the determination of the orientation of the forearm comprises the implementation of a linear or non-linear state estimation filter.

5. The method according to claim 1, wherein said inertial measurement means are arranged on said forearm between an elbow and a wrist.

6. The method according to claim 1, wherein the physical parameters of the forearm comprise a length of the forearm and a radius of the forearm.

7. The method according to claim 6, wherein the torque estimated at said estimating is a torque per mass unit of said forearm given by the formula $$\vec{C_M} = \begin{pmatrix} \frac{R^2}{4} + \frac{L^2}{3} & 0 & 0 \\ 0 & \frac{R^2}{4} + \frac{L^2}{3} & 0 \\ 0 & 0 & \frac{R^2}{2} \end{pmatrix} \times \begin{bmatrix} \frac{d\omega_x}{dt} \\ \frac{d\omega_y}{dt} \\ \frac{d\omega_z}{dt} \end{bmatrix} - \frac{L}{2} g \cos\theta_e \vec{e_n},$$

where $\vec{\omega}$ is the measured angular speed, R the radius of the forearm, L the length of the forearm, $\vec{g}$ the acceleration due to gravity, $\theta_c$ the angle of elevation of the forearm and $\vec{e_n}$ the unit vector normal to the forearm and to the direction of the acceleration due to gravity.

8. The method according to claim 1, wherein said determining comprises the identification of a driving or resisting character of the determined power.

9. The method according to claim 1, being a method for estimating a quantity representative of the physical activity exerted by the upper limb of the person, the method comprising estimating said quantity representative of the physical activity from the determined power.

10. The method according to claim 9, wherein said quantity representative of the physical activity is the energy exerted by the upper limb over a time interval, is determined by adding together the absolute value of each power determined at each instant of said time interval.

11. The method according to claim 9, further comprising comparing said estimated quantity representative of the physical activity with at least one predetermined threshold so as to identify a muscular problem of the upper limb of the person.

12. A non-transitory computer program product comprising code instructions for the execution of a method for estimating the physical activity exerted by an upper limb of a person according to claim 1, when said program is executed on a computer.

13. Storage means readable by computer equipment on which a non-transitory computer program product comprises code instructions for the execution of a method for estimating the physical activity exerted by an upper limb of a person according to claim 1.

14. Equipment for estimating a physical activity exerted by an upper limb of a person comprising data processing means configured to implement:

A module for receiving a measured angular speed of a forearm of said upper limb of said person acquired by inertial measurement means solidly attached to said forearm;

A module for estimating a torque exerted by any muscles of an arm of the upper limb on said forearm as a function of the measured angular speed, of an orientation of said forearm and of physical parameters of said forearm;

A module for determining a power exerted by the upper limb as a function of the estimated torque and of the measured angular speed.

15. The equipment according to claim 14, being a housing comprising the inertial measurement means.

16. The equipment according to claim 15, further comprising means for attaching the housing to the upper limb and communication means.

17. The equipment according to claim 14, being a mobile terminal or a server, adapted to communicate with a housing comprising the inertial measurement means.

18. System comprising the equipment according to claim 17 and at least one housing coupled to said equipment.

* * * * *